United States Patent
Bacon

(10) Patent No.: US 7,225,805 B2
(45) Date of Patent: Jun. 5, 2007

(54) DRUG DISPENSER

(75) Inventor: Raymond John Bacon, Hampshire (GB)

(73) Assignee: Clinical Designs Limited, Emsworth Hampshire (GB)

( * ) Notice: Subject to any disclaimer, the term of this patent is extended or adjusted under 35 U.S.C. 154(b) by 195 days.

(21) Appl. No.: 10/433,861

(22) PCT Filed: Dec. 5, 2001

(86) PCT No.: PCT/GB01/05410

§ 371 (c)(1),
(2), (4) Date: Nov. 3, 2003

(87) PCT Pub. No.: WO02/45783

PCT Pub. Date: Jun. 13, 2002

(65) Prior Publication Data

US 2004/0055596 A1 Mar. 25, 2004

(30) Foreign Application Priority Data

Dec. 5, 2000 (GB) .................................. 0029612.9

(51) Int. Cl.
*A61M 11/00* (2006.01)
*S61M 15/00* (2006.01)

(52) U.S. Cl. .................... 128/200.23; 128/205.23; 128/200.14; 128/203.15

(58) Field of Classification Search ........... 128/200.14, 128/200.23, 200.22, 203.12, 204.23, 203.15; 251/4, 10; 222/402.1, 528, 494; 239/337, 239/576

See application file for complete search history.

(56) References Cited

U.S. PATENT DOCUMENTS

| 3,187,748 | A | 6/1965 | Mitchell et al. | |
|---|---|---|---|---|
| 4,393,884 | A | 7/1983 | Jacobs | |
| 5,826,570 | A | 10/1998 | Goodman et al. | |
| 6,422,234 | B1 * | 7/2002 | Bacon | 128/200.14 |
| 6,866,038 | B2 * | 3/2005 | Bacon | 128/200.23 |
| 7,036,505 | B2 * | 5/2006 | Bacon et al. | 128/203.13 |
| 7,047,964 | B2 * | 5/2006 | Bacon | 128/200.23 |

FOREIGN PATENT DOCUMENTS

| EP | 0461281 | 12/1991 |
|---|---|---|
| WO | 9207600 | 5/1992 |
| WO | 9841254 | 9/1998 |

* cited by examiner

*Primary Examiner*—Justine R. Yu
*Assistant Examiner*—Shumaya Ali
(74) *Attorney, Agent, or Firm*—Alfred A. Fressola; Ware, Fressola, Van Der Sluys & Adolphson LLP

(57) ABSTRACT

A drug dispenser 1 has a hollow body 2 with a housing 6 for a pressurised can 7 containing a drug and its propellant arranged on top of the body. The can has an outlet stem 8 received in a socket 9 in an internal spigot 10. This has a junction with a flexible tube 11, leading to a kink valve pair 12,14. The tube continues on to a second internal spigot 15, having a spray nozzle 16 just within a breathing opening 5. The kink valve pair 12, 14 is formed as a moulding of the tube, with side wings 17. Towards the ends of the wings, they have thinner portions 17.1 at which there are apertures 18 immediately adjacent the tube. The arrangement defines positions at which the tube kinks to close its through bore 19. The thinner portions are provided in two positions, which provide the two kink valves. An intermediate section 20 of the tube, with a predetermined volume is provided between the kink valves.

24 Claims, 7 Drawing Sheets

DRUG DISPENSER

CROSS REFERENCE TO RELATED APPLICATIONS

This application is for entry into the U.S. national phase under §371 for International Application No. PCT/GB01/05410 having an international filing date of Dec. 5, 2001, and from which priority is claimed under all applicable sections of Title 35 of the United States Code including, but not limited to, Sections 120, 363 and 365(c), and which in turn claims priority under 35 USC §119 to Great Britain Patent Application No. 0029612.9 filed on Dec. 5, 2000.

TECHNICAL FIELD

The present invention relates to a dispenser for dispensing drugs in small breathable particles.

BACKGROUND OF THE INVENTION

Increasingly drugs are dispensed as a mist for inhalation. Not only is this used for asthma drugs, but it is used for other drugs as well. Asthma drugs have been dispensed by a nebuliser, which provides a mist for inhalation by successive breaths. Increasingly, nebulisers are being replaced by pressurised metered dose inhalers. The former are bulky, expensive pieces of equipment, whilst the latter are disposable aerosol devices but they suffer from some disadvantages. In particular, inhalers require a deep breath to ensure that the medicament is carried into the lungs. Patients, in particular infants, young children and those with severe symptoms, having weak breathing may be unable to use an inhaler effectively and have to rely on a nebuliser.

Conventionally, aerosol storage devices have utilised a metal can for storage of the contents to be dispensed under pressure contained in the can. However, it is anticipated that in the future metallic cans may be replaced by cans of plastics material or even of glass for specialised applications. Accordingly as used herein the term "can" means not only metallic cans but substitute or equivalent containers of other materials, in particular glass and plastics materials.

SUMMARY OF THE INVENTION

The object of the invention is to provide an improved breathable particle drug dispenser, which utilises aerosol pressure for dispersion of the drug yet which is not limited to dispensing metered doses between which the aerosol storage device requires manual actuation to release a metered dose.

According to a first aspect of the invention there is provided a drug dispensing device for repetitive dispensing on inhalation of a drug released from a pressurised drug source with a can body and a delivery stem, the dispenser comprising:
 a hollow body having:
  a wall enclosing a breath passage within the hollow body,
  an ambient opening to the breath passage,
  a patient breathing opening to the breath passage,
  a can receptor attached to the hollow body for accommodating the can of the pressurised drug source,
  a junction member attached to the hollow body for connection with the dispensing stem of the pressurised drug source and leading delivered drug from the dispensing stem,
 a drug disperser for dispersing the delivered drug towards the patient breathing opening,
 a drug duct from the junction member to the drug disperser,
 a breath detector arranged in the breath passage to be acted on by breath passing therethrough, and
 dose release means operatively connected to the breath detector, the dose release means being so arranged that:
  on inhalation, with the breath detection member detecting such, a dose is released into the drug duct and dispersed from the drug disperser in the patient breathing opening;

the arrangement permitting a small dose of the drug to be repetitively released on each breath by the patient.

According to a second aspect of the invention there is provided a drug dispensing device for repetitive dispensing on inhalation of a drug released from a pressurised drug source with a can body and a delivery stem, the dispenser comprising:
 a hollow body having:
  a wall enclosing a breath passage within the hollow body,
  an ambient opening to the breath passage,
  a patient breathing opening to the breath passage,
  a can receptor attached to the hollow body for accommodating the can of the pressurised drug source,
  a junction member attached to the hollow body for connection with the dispensing stem of the pressurised drug source and leading delivered drug from the dispensing stem,
 a drug disperser for dispersing the delivered drug towards the patient breathing opening,
 a drug duct from the junction member to the drug disperser, and
 a valve in the drug path from the container to the disperser,
 a valve actuator operatively connected to the valve and including a breath detection member arranged in the breath passage to be acted on by breath passing therethrough, the valve and the actuator being so arranged that:
 on inhalation, with the breath detection member detecting such, the valve is opened to allow pressurised drug through a downstream portion of the drug duct and disperse from the drug disperser in the patient breathing opening breathing adapter;

the arrangement permitting a small dose of the drug to be repetitively released on each breath by the patient.

In one series of embodiments, the valve will be a dual in line valve arrangement, the arrangement having:
 an upstream valve,
 a downstream valve and
 an intermediate section of the drug duct between the two valves, the valve and the actuator being so arranged that:
  on inhalation, with the breath detection member detecting such, the downstream valve is opened to allow pressurised drug in the said intermediate section to pass through a downstream portion of the drug duct and disperse from the drug disperser in the patient breathing opening and
  subsequently the upstream valve is opened to allow pressurised drug to pass from an upstream portion of the drug duct into the intermediate section;

the arrangement permitting a small dose of the drug metered by the intermediate section to be repetitively released therefrom on each breath by the patient.

Particularly where, as described below, the dual in line valve arrangement is mechanically actuated by action of breath on a flap or piston, it is on exhalation, with the breath detection member detecting such, that the upstream valve is opened for passage of the pressurised drug into the intermediate section.

Alternatively, and particularly where, as also described below, the dual in line valve arrangement is electrically operated via breath detection by a transducer, it is during the inhalation or during overlap between inhalation and exhalation, that the upstream valve is opened for passage of the pressurised drug into the intermediate section.

Conveniently, the intermediate section of the drug duct will have a predetermined metering volume.

Preferably, the up- and down-stream valves are mechanically linked together, with one being closed when the other is open and vice versa; and usually the valves will be adapted to be both closed together in a mid-position of their mechanical linkage.

Alternatively to the series of embodiments having two valves, a single valve can be employed with the valve actuator includes means for closing the valve a predetermined time after its opening on inhalation, the arrangement being such that the predetermined dose of drug is released during the predetermined period under pressure from drug source.

Normally the device will include a breathing adapter at the patient breathing opening for guiding the delivered drug to a patient's airway, and the breathing adapter will be one of a group comprising a mouthpiece, a face mask, an adapter for a mouthpiece, an adapter for a face mask or a spacer chamber.

In a two valve embodiment, the up- and down-stream valves can be electro-magnetic valves and the breath detection member can be a transducer arranged in the breath passage. Also in the single valve embodiment, the valve can be an electro-mechanical valve, with the breath detection member being a transducer arranged in the breath passage and the valve actuator including a control circuit adapted and arranged to open the valve for a predetermined period on detection of inhalation and then to close the valve.

The transducer can be a pressure transducer, detecting inhalation by fall in static pressure or increase in dynamic pressure (velocity head) on the ambient side of the transducer (or fall of dynamic pressure on the breathing adapter side) and exhalation by increase in static pressure decrease in dynamic pressure on the ambient side of the transducer (or increase of dynamic pressure on the breathing adapter side). Again, the transducer can be a flow meter having a member movable in the direction of flow through the tube. However, it is preferably a temperature transducer, detecting inhalation by fall in temperature and exhalation by increase in temperature. Conveniently a counter is arranged to be incremented by successive indications of breaths given by the transducer for counting the number of breaths and drug dispersals controlled by the valve arrangement.

In other embodiments, the up- and down-stream valves are mechanical valves and the breath detection member is a movable flap or a slidably mounted piston arranged in the breath passage to be moved in accordance with breath past it and linked to the valves for their actuation.

Preferably, the breath detecting flap is a pivotally mounted to be movable by the patient's breathing between an inhalation position and an exhalation position and the valves—or their actuation members—are pivotally operated, the flap and the valves or their actuation members being connected together to open the upstream valve (the downstream valve being closed) on exhalation and movement of the flap away from the breathing adapter to fill the intermediate section with drug and opening the downstream valve (the upstream valve being closed) on inhalation and movement of the flap towards the breathing adapter to dispense the drug.

Whereas variants can be envisaged, such as the use of a double pinch valve in a rocker format or other rocker valves; in the preferred embodiments, the valves are kink valves, that is to say valves having flexible tubes which are arranged to kink to close the valve and un-kink to open the valve.

In one embodiment, the up- and down-stream portions of the drug duct are arranged to connect to the respectively opposite ends of the intermediate section via the kink valves, the said portions both being to the same side of the intermediate section and describing a squat Δ therewith, and the intermediate section being connected directly to the flap for movement along the breath passage with the flap.

In another embodiment, the up- and down-stream portions of the drug duct are arranged to connect to the respectively opposite ends of the intermediate section via the kink valves, the said portions being on opposite sides of the intermediate section and describing a Z therewith, and the intermediate section being crankedly connected to the flap for movement transversely of the breath passage with movement of the flap therealong.

Preferably, the drug duct has a volume between the junction member and the valve corresponding to a plurality of the doses released on a plurality of inhalations for use with multiple doses from a metered dose pressurised drug source, whereby such plural depressions charges the duct with a determined quantity of drug for a plurality of inhalations.

According to another aspect of the invention, a drug dispenser comprises a dispensing device of the first aspect in combination with a pressurised drug source, the can body being accommodated in the housing and the delivery stem connected to the junction member.

It is envisaged that the dose released per breath may be adjustable, by adjusting the metering volume of the intermediate section of the drug duct.

Normally the container will be provided with a release valve whereby dispensing of the drug can be stopped and started at will. However, the container may be a metered dose container.

According to a further embodiment, there is provided A drug dispensing device for repetitive dispensing on inhalation of a drug released from a pressurised drug source with a can body, metered dose release drug release valve and a delivery stem, the dispenser comprising:

a hollow body having:
    a wall enclosing a breath passage within the hollow body,
    an ambient opening to the breath passage,
    a patient breathing opening to the breath passage,
    a can receptor attached to the hollow body for accommodating the can of the pressurised drug source,
    a junction member attached to the hollow body for connection with the dispensing stem of the pressurised drug source and leading delivered drug from the dispensing stem,
a drug disperser for dispersing the delivered drug towards the patient breathing opening,
a drug duct from the junction member to the drug disperser, and a breath detection transducer arranged in the breath passage to be acted on by breath passing therethrough, a can actuator operatively connected to the body for moving the can towards the junction member, the can actuator being so arranged that:

on inhalation, with the breath detection member detecting such, the can is moved to operate its metered dose valve for allowing pressurised drug to flow to the drug disperser and to disperse from the drug disperser in the patient breathing opening;

the arrangement permitting a small dose of the drug to be repetitively released on each breath by the patient.

BRIEF DESCRIPTION OF THE DRAWINGS

To help understanding of the invention, a specific embodiment thereof will now be described by way of example and with reference to the accompanying drawings, in which.

DETAILED DESCRIPTION

Figure 1:
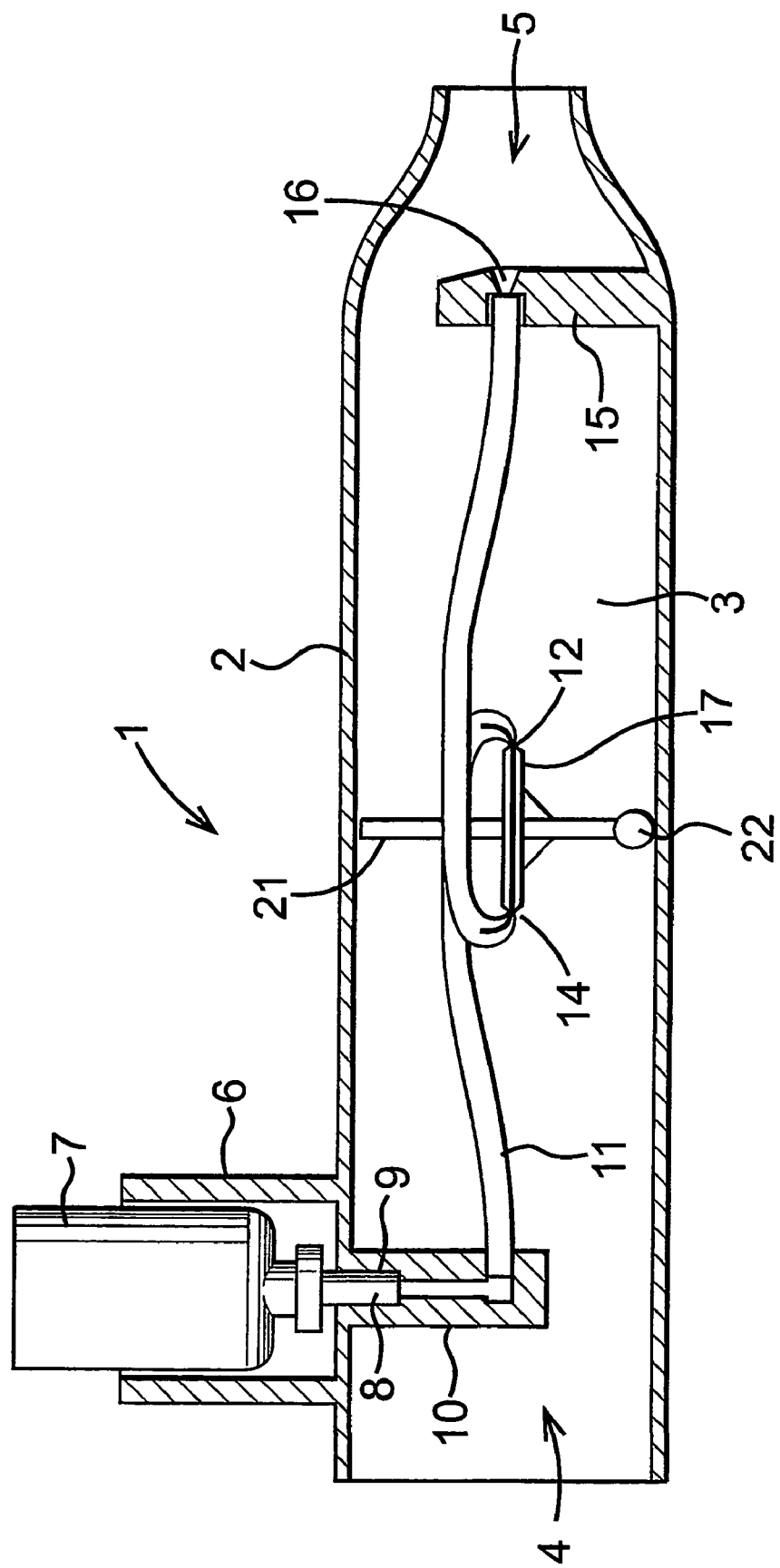
FIG. 1 is a cross-sectional side view of a dispenser according to the invention.
Figure 2:
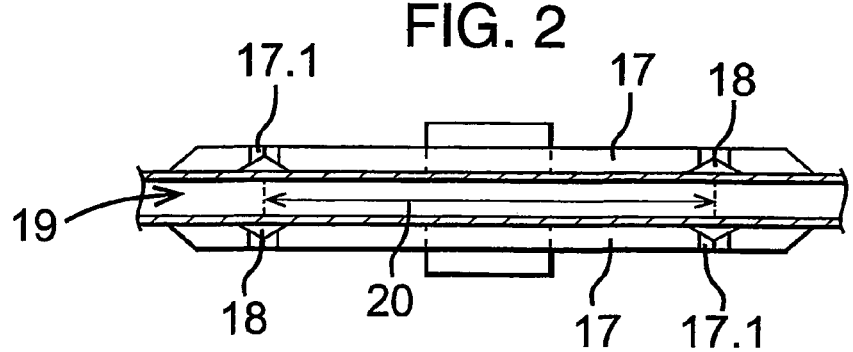
FIG. 2 is a scrap, plan cross-sectional view of a kink valve portion of a drug duct of the dispenser of FIG. 1.
Figure 3:
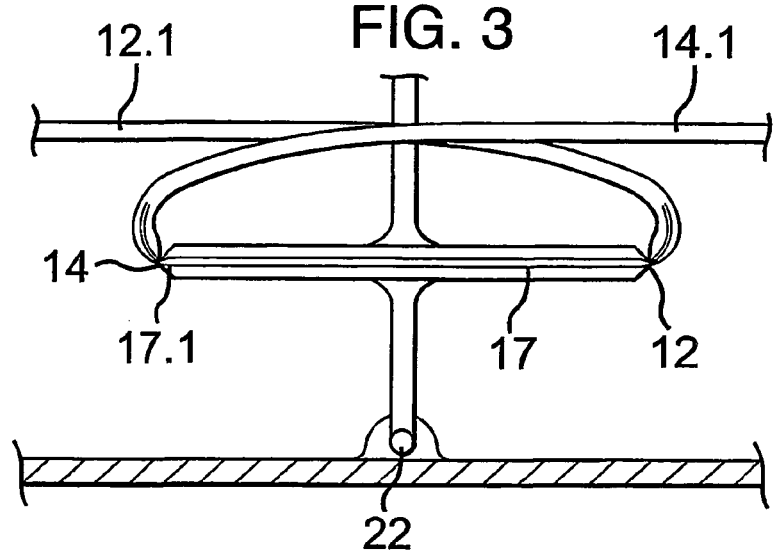
FIG. 3 is a scrap cross-sectional side view of the kink valve portion of the drug duct, with both valves closed.

Referring to FIGS. 1 to 4, the drug dispenser 1 has a hollow body 2 providing a breath passage 3, with an ambient opening 4 and a patient breathing opening 5. A housing 6 for receving a pressurised can 7 containing a drug and its propellant is arranged on top of the body. The can has an outlet stem 8 received in a socket 9 in an internal spigot 10. This has a junction with a flexible tube 11, leading to a kink valve pair 12,14. The tube continues on to a second internal spigot 15, having a spray nozzle 16 just within the breathing opening 5.

The kink valve pair 12, 14 is formed as a moulding of the tube, with side wings 17. Towards the ends of the wings, they have thinner portions 17.1 at which there are apertures 18 immediately adjacent the tube. The arrangement, which is similar to that in my International Application No. PCT/GB01/03313, defines positions at which the tube kinks to close its through bore 19. The thinner portions are provided in two positions, which provide the two kink valves. An intermediate section 20 of the tube, with a predetermined volume is provided between the kink valves.

At the intermediate section, the tube 11 is clipped to flap 21, pivoted at its end 22 to the side wall of the body. As a patient breathes through the device, the flap is moved by the action of the breath on it. Specifically, as the patient inhales, the flap moves towards the breathing opening and as the patient exhales the flap moves towards the ambient opening. The flap has clearance with the passage such that it does not significantly obstruct the air passage, but at the same time the inhalation and exhalation positively moves the flap. The kink valve pair moves with the flap.

Figure 4:
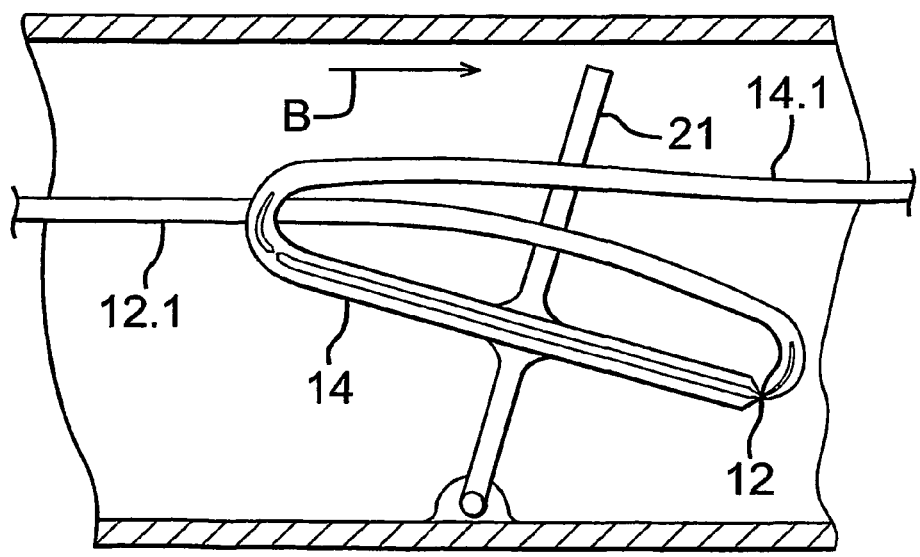
FIG. 4 is a view similar to FIG. 3 with a flap displaced on inhalation, the downstream valve open for drug release and the upstream valve closed.
Figure 5:
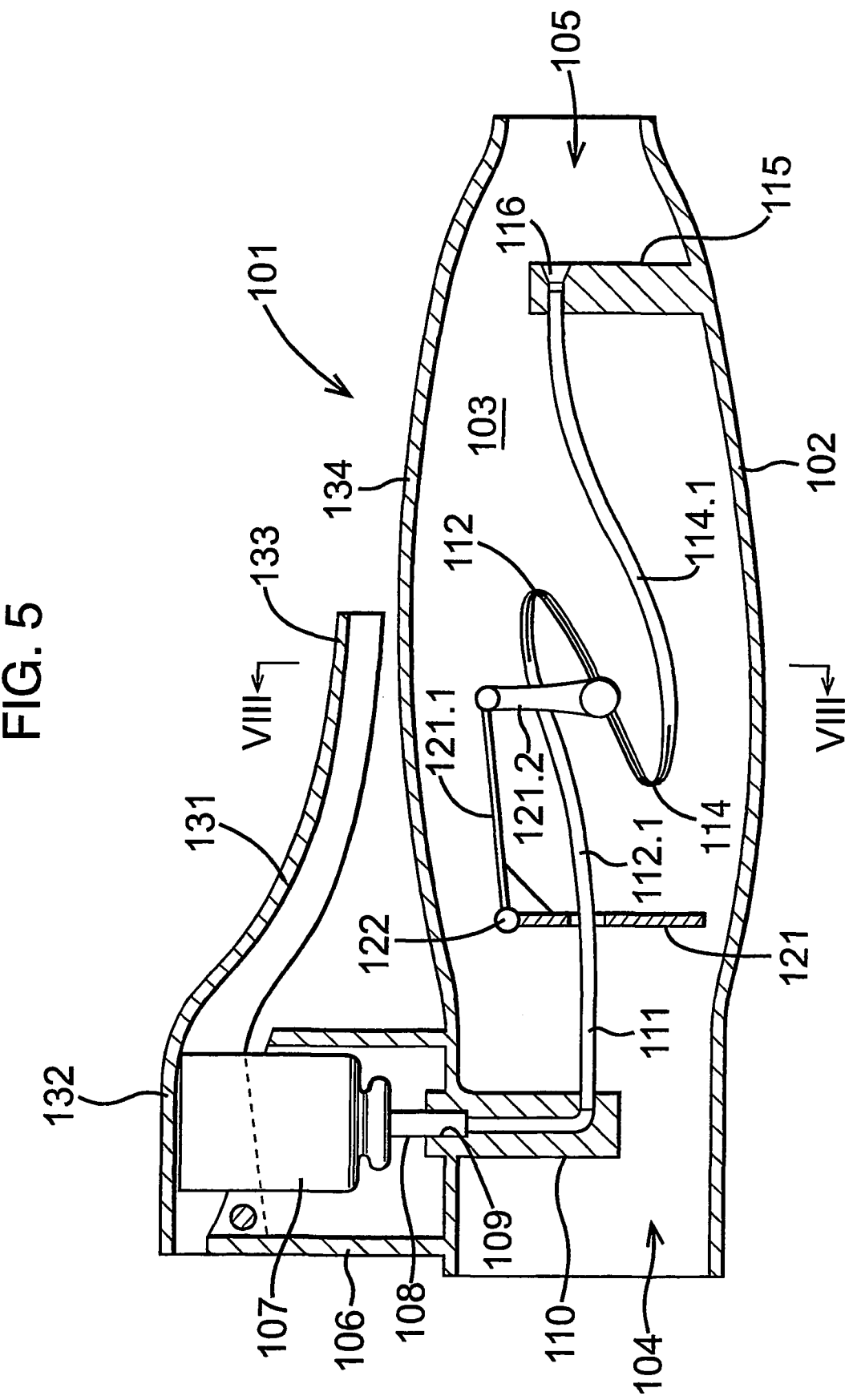
FIG. 5 is a view similar to FIG. 1 of a second dispenser according the invention.
Figure 6:
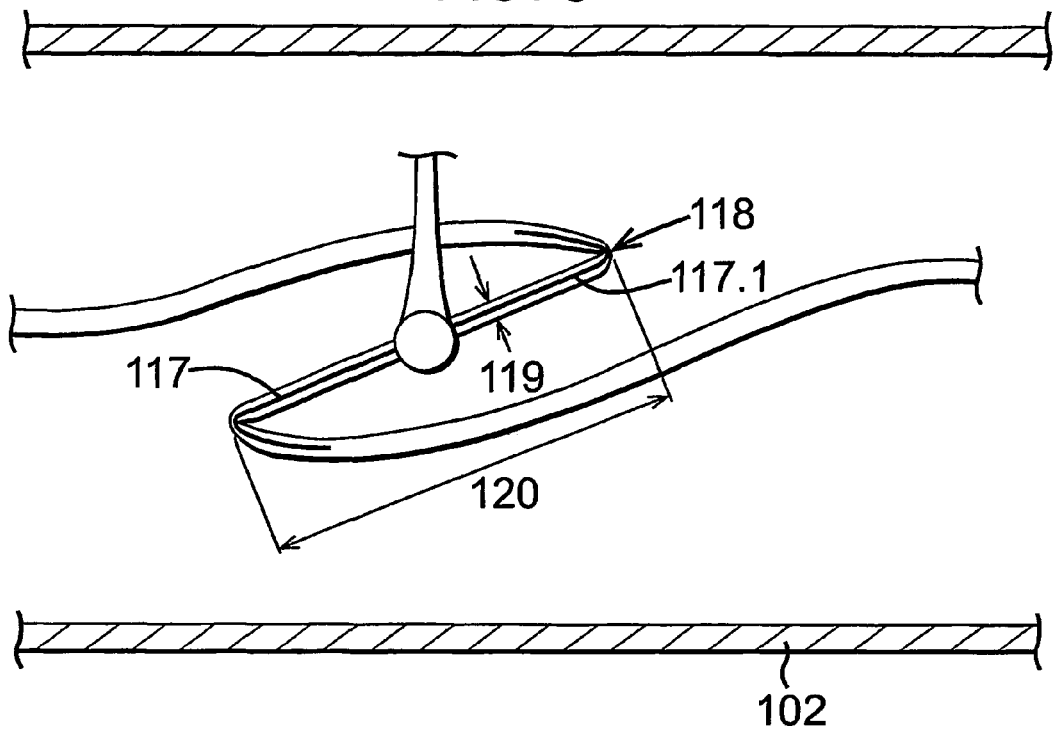
FIG. 6 is a view similar to FIG. 4 of the second dispenser.
Figure 7:
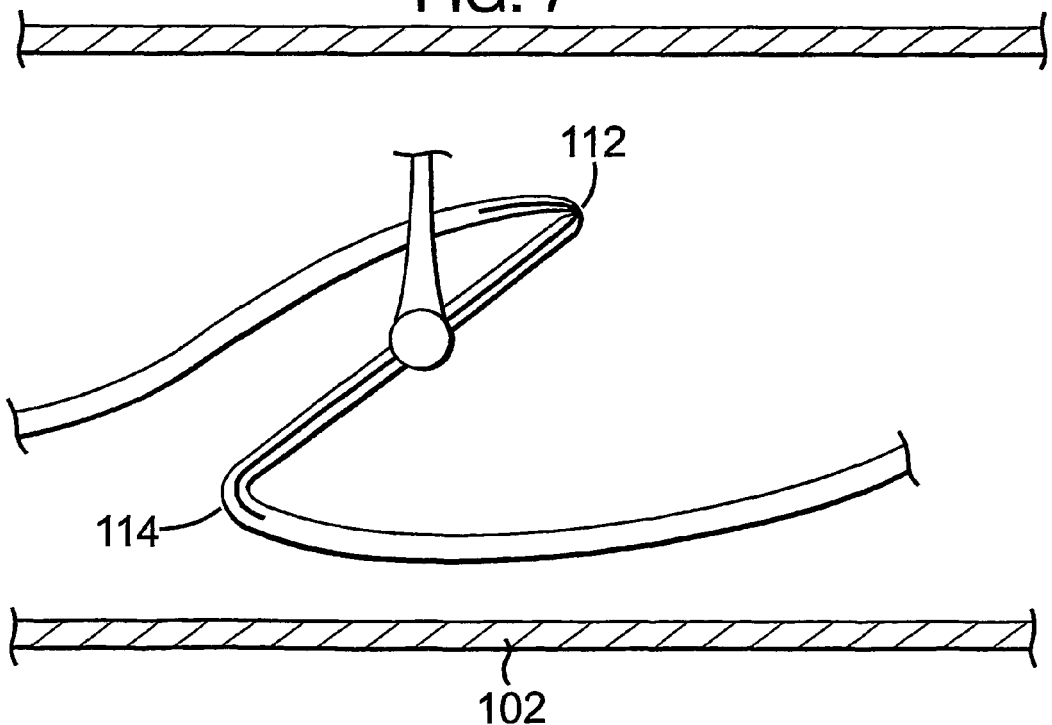
FIG. 7 is a view similar to FIG. 5 of the second dispenser.
Figure 8:
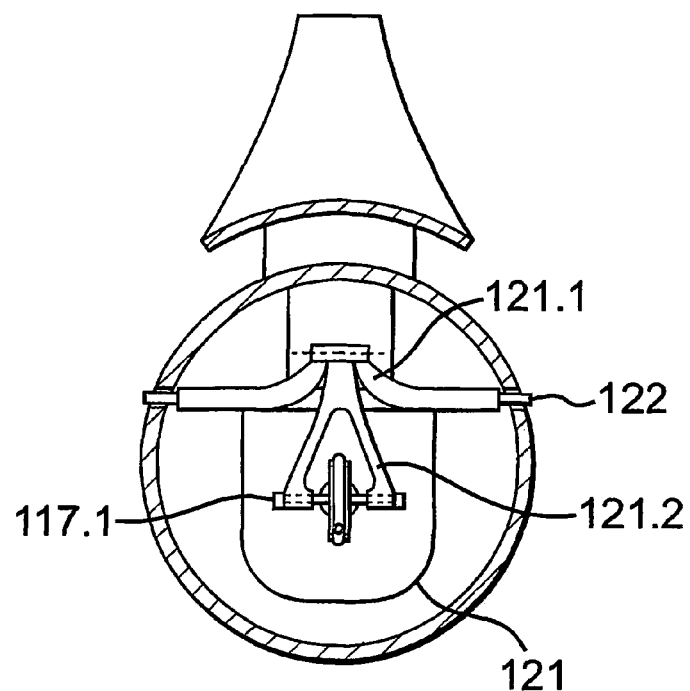
FIG. 8 is a cross-sectional end view on the line VIII—VIII of the second dispenser.

Referring to FIG. 4, the inhalation action is shown. The air to be breathed in moves in the direction of the arrow B and the flap is drawn along with it. The intermediate section 20 is tilted, moving the valve 12 down to the pivot side of the passage. This action tightens the length of tube 12.1 leading back to the junction with the can. This causes the upstream kink valve to tighten and remain closed. The down stream kink valve 14 moves closer to the spray nozzle 16. The length of tube 14.1 between these two is slackened, causing the kink valve 14 to straighten somewhat and open. Thus the drug and pressurised propellant within the intermediate section 20 is released.

On exhalation, the flap 21 is moved back in the opposition direction to that shown in FIG. 4, closing the downstream valve 14 and opening the upstream valve 12. Thus pressurised propellant and drug in the upstream portion 12.1 of the tube is able to pass into the intermediate section, for dispensing when the cycle is repeated.

To charge the upstream tube portion 12.1 in the first instance, the can is depressed. Where it has a metered dose release valve, a prescribed number of depression and releases will release a known quantity of the drug into the tube. Successive breathing through the tube will then steadily dispense the drug. Normally the device will be used for a number of breaths exceeding the theoretical number corresponding to the quantity of drug released, to ensure that the upstream tube is completely emptied.

Where the known quantity of drug to be dispensed is large in comparison with the volume of the normal upstream tube portion, this volume can be increased by use of a larger diameter tube for part of its length. The device can be designed with the upstream tube volume being defined, whereby it completely fills with the required dose. Thus filling of the tube with an excess number of depressions of the can, as opposed to use of a determined number of depressions, can be used to release from the can the prescribed dosage to be inhaled.

It will be appreciated that the two kink valves are mechanically linked, with one being closed when the other is open and vice versa. At no time are both valves open together and indeed both are closed when the valve arrangement is in mid-position.

Turning on to FIGS. 5 to 8, the dispenser 101 there shown differs as regards it kink valve arrangement and the arrangement for releasing the drug. The dispenser body 102 has:

a breath passage 103,
an ambient opening 104,
a patient breathing opening 105,
a can housing 106,
a drug can 107,
a can outlet 108,
a socket 109 & internal spigot 110,
a flexible tube 111 with an upstream portion 112.1 & and a downstream portion 114.1,
a kink valve pair 112,114,
a second internal spigot 115 & spray nozzle 116 tube side wings 117, thinner portions 117.1 and apertures 118 a through bore 119 and a tube intermediate section 120 and an end 122 pivoted flap 121.

These features have direct equivalents with the similarly numbered features in the first embodiment.

However the flap and kink valves are differently arranged. The flap is pivoted at a position spaced from the side of the breath passage 103 and carries an crank 121.1 which extends along the breath passage. At its distal end, the crank is pivotally connected to a Y piece 121.2, itself pivotally connected to trunnions 117.1 on the intermediate tube section 120. The arrangement is such that at rest (FIG. 6) both kink valves 112,114 are closed. On inhalation (FIG. 7), the intermediate section 120 is lifted and turned slightly anticlockwise as the upstream portion 112.1 tightens. This keeps the upstream valve 112 closed, but opens the downstream valve 114. The drug is dispensed via the spray nozzle 116 from the intermediate section 120. Similarly exhalation allows recharging of the intermediate section from the upstream tube portion 112.1.

The arrangement for charging the upstream tube portion differs in that the can is a non-metered dose can. A release lever 131 is pivoted to the can housing 106, with an abutment area 132 contacting the can and a handle 133 extending over the central region 134 of the body 102. Gripping of the dispenser can be such that the handle is depressed to release drug and propellant continuously into the upstream tube portion. However, since one or other (or both) of the kink valves 112,114 is always closed, the drug is released only on inhalation. The prescribed dose can be inhaled by keeping the handle depressed for a specific number of breaths, which dispense a specific quantity of drug, corresponding to the volume of the intermediate section times the number of inhalations. As with the first embodiment, the upstream portion of the tube can be emptied of drug by continued breathing through the device after release of the handle 133.

Figure 9:
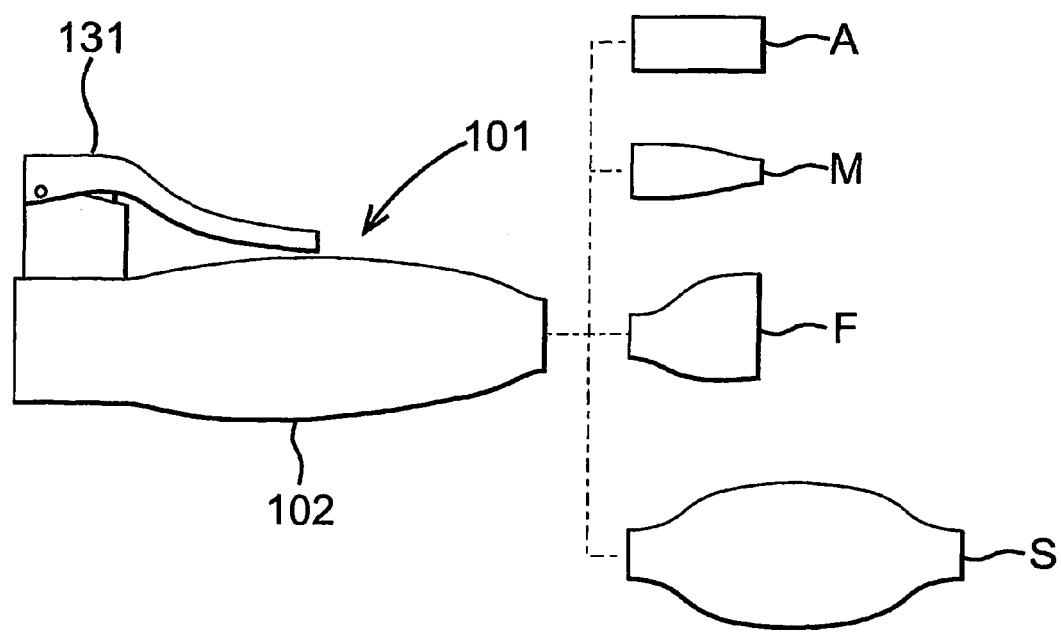
FIG. 9 is a diagrammatic side view of the second dispenser with alternative patient adapters.

Turning to FIG. 9, the second dispenser—and indeed the first—will normally be used in conjunction with a mouthpiece M or a facemask F or a spacer S or an adapter A for any of these. These fit the body 102 at the opening 105 and are provided for positively guiding the delivered drug to a patient's airway.

Figure 10:
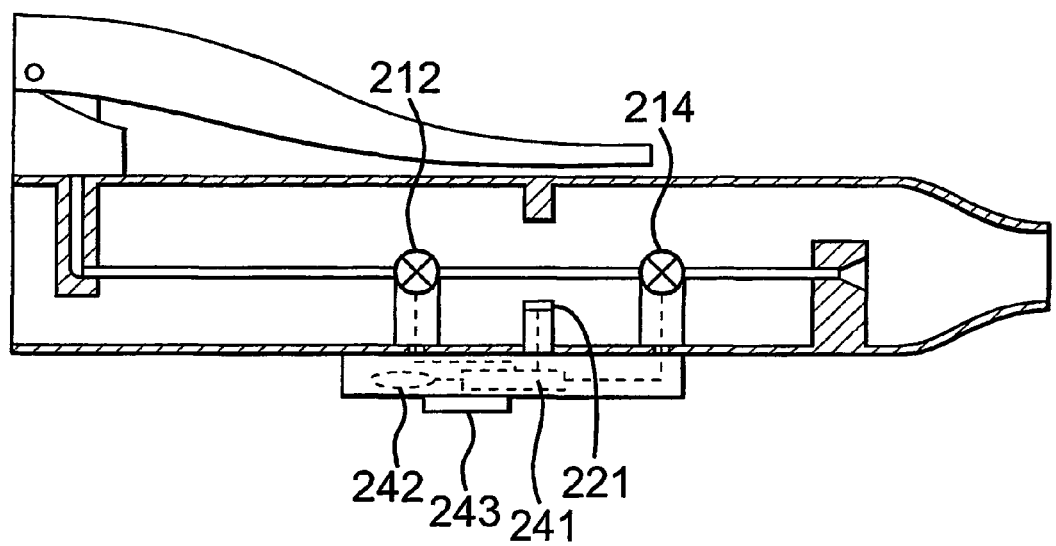
FIG. 10 is a view similar to FIG. 5 of a third dispenser according to the invention.

Turning now to FIG. 10, an electronic version of the second embodiment is shown. In place of kink valves, it has two electromagnetic valves 212, 214. In place of the flap its has a temperature transducer 221, typically a thermocouple. These three are connected to a control circuit 241, powered by a cell 242 and having a counter associated with it. The temperature of the transducer falls with inhalation and rises with exhalation. This can be utilised to program the control circuit to open the downstream valve 214 only on inhalation and open the upstream valve 212 only on exhalation. Alternatively, bearing in mind the ability to meter a dose by timing, as described in respect of FIG. 11 below, the downstream valve 214 can be opened and closed again during the same inhalation and indeed the upstream valve opened and closed again to charge the intermediate section also during the same inhalation or possibly overlapping the same inhalation and a subsequent exhalation. This sequence can all be triggered by an inhalation threshold of air movement through the breath passage, whereby detection of exhalation is not relied upon.

The device includes a counter 243, which displays the number of breathing/dispensing cycles so that the prescribed quantity of drug can be dispensed. However, in other respects, the use of the device is exactly analogous to the that of the mechanical/kink-valve embodiment.

Figure 11:
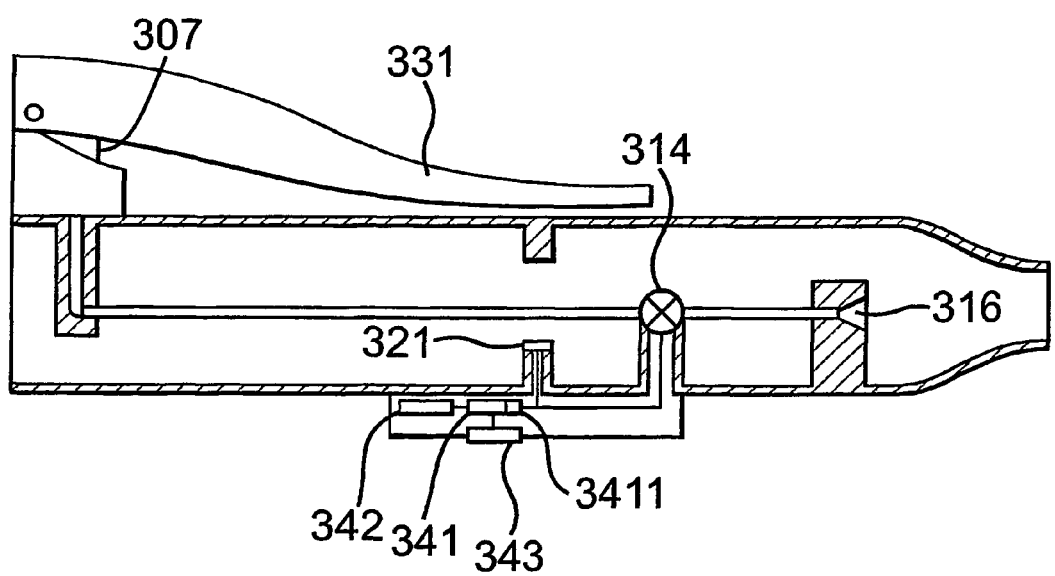
FIG. 11 is a view similar to FIG. 5 of a fourth dispenser according to the invention.

Referring now to FIG. 11, the dispenser there shown differs from that of FIG. 10 in having a single electromechanical valve 314, with the can 307 being a continuous release can. The transducer 321, controller 341, cell 342 and the counter display 343 are physically arranged similarly to those of FIG. 10, but the controller is differently programmed and includes a timer 3411 circuit. The programming is such that on an inhalation signal being received from the transducer, the controller causes the valve 314 to open, but only for a time limited to that required for dispensing a dose of drug from the spray nozzle 316 metered by the timer, typically a fraction of a second. On expiry of this period, the controller closes the valve. The opening and closing of the valve for dispensing of the drug occurs entirely within the inhalation period and throughout the dispensing, uninhibited flow of drug from the can occurs, with the handle 331 depressing the can for opening of its stem valve (not shown). The dispenser continues to be used until the count shown on the counter for a prescribed dosage is reached. Where the user is not being supervised, as of a child by a mother, the counter display can be augmented by an audio or visual alarm such as an LED. The controller can be provided with keys for setting the number of inhalations to be counted before alarming.

Figure 12:
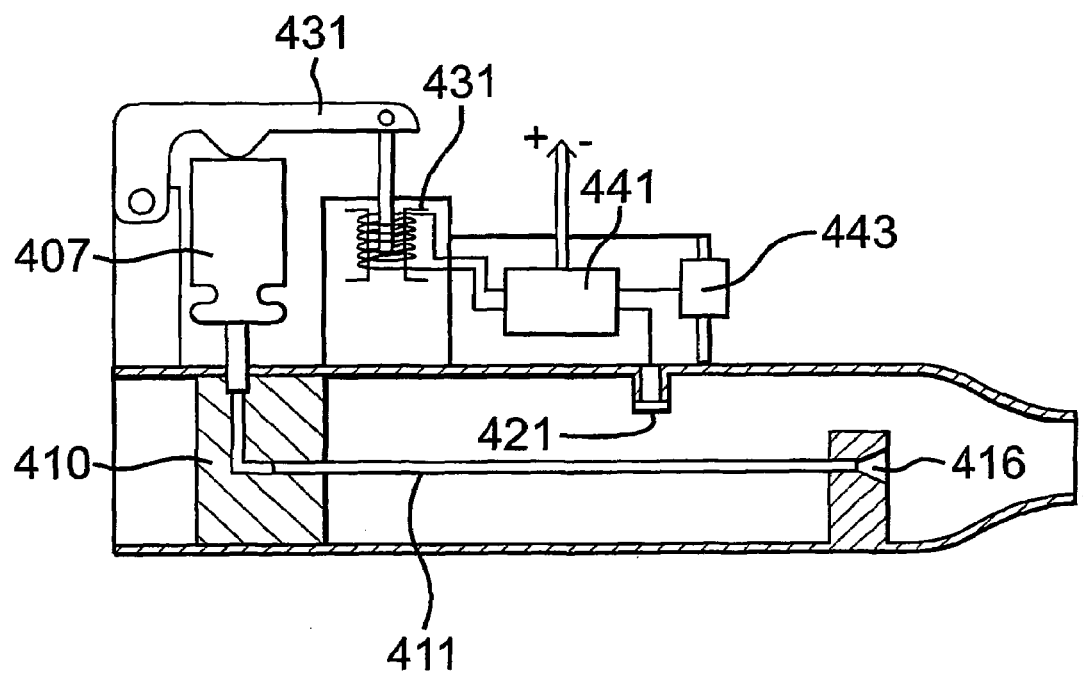
FIG. 12 is a view similar to FIG. 5 of a fifth dispenser according to the invention.

Referring onto FIG. 12, the dispenser there shown differs in having a valve (not shown) only in the can 407, which is a metered dose can. It has a can junction 410, connected to a spray nozzle 416 by a drug duct 411, and a transducer 421 with a controller 441 and a counter display 443. This dispenser has an external power supply for actuating a solenoid 451 on inhalation under control of the controller. The solenoid acts on an arm 431 similar to the handle 331 for depressing the can and releasing a dose metered by the can's internal valve. Thus on successive inhalations, up to a prescribed count, the can is depressed and a dose is inhaled.

Figure 13:
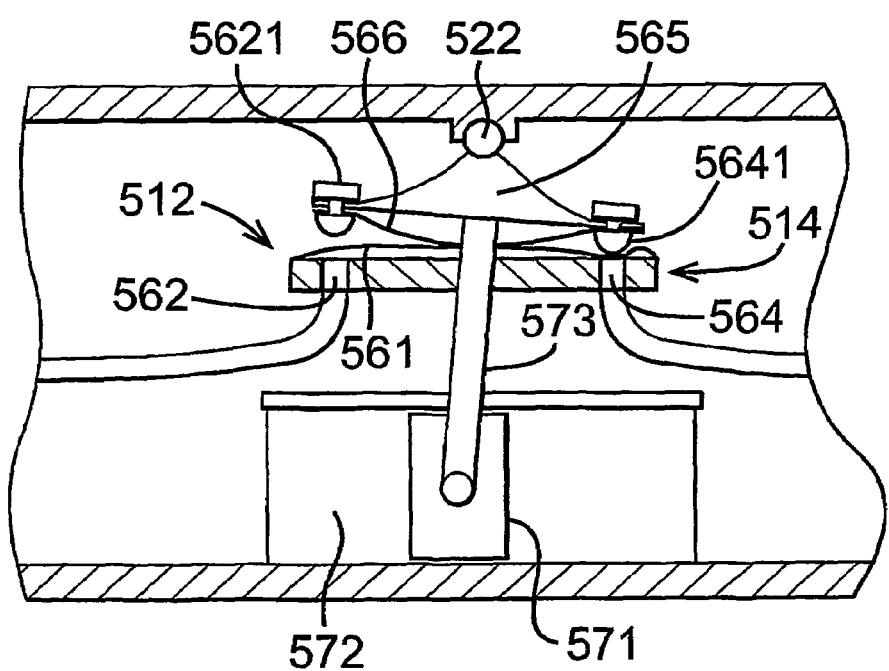
FIG. 13 is a side view of a valve variant for the dispenser of FIG. 1.

The invention is not intended to be restricted to the details of the above described embodiments. For instance a valve and actuator variant for the dispenser of FIG. 1 is shown in FIG. 13. The valves 512,514 there shown are pinch valves having a diaphragm 561 arranged to close either of a pair of orifices 562,564 under the action of a rocker 565 having a pair of pinch fingers 5621,5641. These are normally biased by leafs 566 to close their orifices and lifted by the rocker 565. The latter is pivoted at 522 and actuated by a piston 571 in a cylinder 572, which is open to the breath passage at its respective ends, whereby inhalation pressure differential across the cylinder drives the piston in one direction and exhalation drives it the other way. A linkage 573 connects the piston to the rocker for actuation of the valve. Such a valve can be electrically actuated by a solenoid in place of the piston and cylinder.

The invention claimed is:

1. A drug dispensing device for repetitive dispensing on successive inhalations of a drug released from a pressurised drug source with a can body, a delivery stem and a valve which is normally open in use of the device, the dispenser comprising:

a hollow body having:
   a wall enclosing a breath passage within the hollow body,
   an ambient opening to the breath passage,
   a patient breathing opening to the breath passage, a relatively broad can receptor attached to the hollow body for accommodating the can of the pressurised drug source, a junction member attached to the hollow body at the can receptor for connection with the dispensing stem of the pressurised drug source and leading delivered drug from the dispensing stem, the junction member having a relatively narrow socket for receiving the dispensing stem, a drug disperser for dispersing the delivered drug towards the patient breathing opening, a drug duct from the junction member to the drug disperser, and repetitive dose release means comprising:

at least one valve in the drug duct from the container to the disperser for releasing a dose to the drug disperser, a breath detection member arranged in the breath passage to be acted on by breath passing therethrough and a valve actuator operatively connected to the breath detection member and the valve both for opening the valve on each successive inhalation to release a dose and for closing the valve after the release for recharging of the drug duct upstream of the valve in preparation for release of the next dose, the valve and the actuator being so arranged that:

on inhalation, with the breath detection member detecting such, the valve is opened to allow pressurised drug through a downstream portion of the drug duct and disperse from the drug disperser in the patient breathing opening;

the arrangement permitting a small dose of the drug to be repetitively released on each breath by the patient.

2. A drug dispensing device according to claim 1, including a breathing adapter at the patient breathing opening for guiding the delivered drug to a patient's airway, the breathing adapter being one of a group comprising a mouthpiece, a face mask, an adapter for a mouthpiece, an adapter for a face mask or a spacer chamber.

3. A drug dispensing device according to claim 1, wherein the valve is a dual in line valve arrangement having:

an upstream valve, a downstream valve and an intermediate section of the drug duct between the two valves, the valve and the actuator being so arranged that:

on inhalation, with the breath detection member detecting such, the downstream valve is opened to allow pressurised drug in the said intermediate section to pass through a downstream portion of the drug duct and disperse from the drug disperser in the patient breathing opening and subsequently the upstream valve is opened to allow pressurised drug to pass from an upstream portion of the drug duct into the intermediate section;

the arrangement permitting a small dose of the drug metered by the intermediate section to be repetitively released therefrom on each breath by the patient.

4. A drug dispensing device according to claim 3, wherein the device is so arranged that it is on exhalation, with the breath detection member detecting such, that the upstream valve is opened for passage of the pressurised drug into the intermediate section.

5. A drug dispensing device according to claim 3, wherein the device is so arranged that it is during the inhalation or during overlap between inhalation and exhalation, that the upstream valve is opened for passage of the pressurised drug into the intermediate section.

6. A drug dispensing device according to claim 3, wherein the up-and down-stream valves are mechanically linked together, with one being closed when the other is open and vice versa.

7. A drug dispensing device according to claim 6, wherein the valves are adapted to be both closed together in a mid-position of their mechanical linkage.

8. A drug dispensing device according to claim 3, wherein the up- and down-stream valves are electro-magnetic valves and the breath detection member is a transducer arranged in the breath passage.

9. A drug dispensing device according to claim 8, wherein the transducer is a temperature transducer, detecting inhalation by fall in temperature and exhalation by increase in temperature.

10. A drug dispensing device according to claim 8, wherein the transducer is a pressure transducer, detecting inhalation by fall in static pressure or increase in dynamic pressure on the ambient side of the transducer (or fall of dynamic pressure on the breathing adapter side) and exhalation by increase in static pressure decrease in dynamic pressure on the ambient side of the transducer (or increase of dynamic pressure on the breathing adapter side).

11. A drug dispensing device according to claim 8, wherein the transducer is a flow meter having a member movable in the direction of flow through the tube.

12. A drug dispensing device according to claim 8, including a counter arranged to be incremented by indications of breaths given by the transducer for counting the number of breaths and drug dispersals controlled by the valve arrangement.

13. A drug dispensing device according to claim 3, wherein the up-and down-stream valves are mechanical valves arid the breath detection member is a movable flap or a slidably mounted piston arranged in the breath passage to be moved in accordance with breath past it and linked to the valves for their actuation.

14. A drug dispensing device according to claim 13, wherein the breath detector is a pivotally mounted flap movable by the patient's breathing between an inhalation position and an exhalation position and the valves—or their actuation members—are pivotally operated, the flap and the valves or their actuation members being connected together to open the upstream valve (the downstream valve being closed) on exhalation and movement of the flap away from the breathing adapter to fill the intermediate section with drug and opening the downstream valve (the upstream valve being closed) on inhalation and movement of the flap towards the breathing adapter to dispense the drug.

15. A drug dispensing device according to claim 14, wherein the valves are kink valves, that is to say valves having flexible tubes which are arranged to kink to close the valve and un-kink to open the valve.

16. A drug dispensing device according to claim 15, wherein the up- and down-stream portions of the drug duct are arranged to connect to the respectively opposite ends of the intermediate section via the kink valves, the said portions being on opposite sides of the intermediate section and describing a Z therewith, and the intermediate section being crankedly connected to the flap for movement transversely of the breath passage with movement of the flap therealong.

17. A drug dispensing device according to claim 15, wherein the up- and down-stream portions of the drug duct are arranged to connect to the respectively opposite ends of the intermediate section via the kink valves, the said portions both being to the same side of the intermediate section and describing a squat Δ therewith, and the intermediate section being connected directly to the flap for movement along the breath passage with the flap.

18. A drug dispensing device according to claim 13, wherein the up- and down-stream valves are comprised in a rocker valve arrangement, having up- and down-stream pinch vales actuated by a rocker, itself actuated by a piston slidably accommodated in a cylinder open at both ends to the breath passage for inhalation pressure to move it one way and exhalation pressure to move it the other way, for corresponding opening of the pinch valves.

19. A drug dispenser according to claim 13, wherein the pressurised drug source has a release valve arranged to dispense drug continuously whilst the can and the delivery stem remain depressed towards each other, whereby the quantity of drug dispensed whilst the can is depressed corresponds to the quantity of drug per inhalation times the number of inhalations.

20. A drug dispensing device according to claim 3, wherein the drug duct has a volume between the junction member and the valve corresponding to a plurality of the doses released on a plurality of inhalations for use with multiple doses from a metered dose pressurised drug source, whereby such plural depressions charges the duct with a determined quantity of drug for a plurality of inhalations.

21. A drug dispensing device according to claim 1, wherein the valve is a single valve and the valve actuator includes means for closing the valve a predetermined time after its opening on inhalation, the arrangement being such that the predetermined dose of drug is released during the predetermined period under pressure from drug source.

22. A drug dispensing device according to claim 21, wherein:
   the single valve is an electro-mechanical valve,
   the breath detection member is a transducer arranged in the breath passage and
   the valve actuator includes a control circuit adapted and arranged to open the valve for a predetermined period on detection of inhalation and then to close the valve.

23. A drug dispenser comprising a dispensing device according to claim 1 in combination with a pressurised drug source, the can body being accommodated in the receptor and the delivery stem being connected to the junction member.

24. A drug dispenser according to claim 23, wherein the pressurised drug source has a metered dose valve for releasing a predetermined drug dose on each depression of the delivery stem and the can towards each other.

* * * * *

UNITED STATES PATENT AND TRADEMARK OFFICE
CERTIFICATE OF CORRECTION

| | | |
|---|---|---|
| PATENT NO. | : 7,225,805 B2 | Page 1 of 1 |
| APPLICATION NO. | : 10/433861 | |
| DATED | : June 5, 2007 | |
| INVENTOR(S) | : Bacon | |

It is certified that error appears in the above-identified patent and that said Letters Patent is hereby corrected as shown below:

Column 10, line 37, claim 13, line 3, please replace the word "arid" with --and--.

Column 11, line 9, claim 18, line 4, please replace the word "vales" with --valves--.

Signed and Sealed this

Eighteenth Day of September, 2007

JON W. DUDAS
*Director of the United States Patent and Trademark Office*